US00PP19575P3

(12) United States Plant Patent
Sisternes

(10) Patent No.: US PP19,575 P3
(45) Date of Patent: Dec. 16, 2008

(54) ORANGE TREE NAMED 'ALVARINA'

(50) Latin Name: *Citrus sinensis*
Varietal Denomination: Alvarina

(76) Inventor: Alvaro Sanchis Sisternes, Avda. Cortes Valencianas 100, 46650 Canals, Valencia (ES)

( * ) Notice: Subject to any disclaimer, the term of this patent is extended or adjusted under 35 U.S.C. 154(b) by 2 days.

(21) Appl. No.: 11/705,713

(22) Filed: Feb. 14, 2007

(65) Prior Publication Data

US 2007/0192914 P1 Aug. 16, 2007

(30) Foreign Application Priority Data

Feb. 16, 2006 (ES) ..... 20064641

(51) Int. Cl.
*A01H 5/00* (2006.01)

(52) U.S. Cl. ..... Plt./202
(58) Field of Classification Search ..... Plt./202
See application file for complete search history.

(56) References Cited

PUBLICATIONS

UPOV–ROM GTITM, Plant Var Database 2007/05, GTI Jouve Retrieval Software, Citation for Citrus 'Alvarina', one page.*

* cited by examiner

*Primary Examiner*—Kent L. Bell
*Assistant Examiner*—June Hwu
(74) *Attorney, Agent, or Firm*—Buchanan Ingersoll & Rooney PC

(57) ABSTRACT

A new and distinct *Citrus* cultivar is provided which is capable of forming attractive large pleasantly tasting fruit having a light yellow-orange external coloration. The fruit when compared to that of the 'Valencia Late' Sweet Orange Cultivar (non-patented in the United States) is lighter in coloration, generally more flattened, commonly possesses a greater diameter, and peels more readily. Also, the leaves tend to be larger, generally more rounded, and less elongated than those of the 'Valencia Late' cultivar. The fruit matures for consumption at approximately the same time as that of the 'Valencia Late' cultivar. The new cultivar is well suited for the commercial product of a late-maturing fruit crop.

3 Drawing Sheets

Botanical/commercial classification: *Citrus sinensis*/Orange Tree.
Varietal denomination: cv Alvarina.

BACKGROUND OF THE NEW VARIETY

*Citrus* crops including *Citrus sinensis* Sweet Oranges are important to the agricultural economy in many parts of the world. Among *Citrus* plants commonly grown in California and Texas, U.S.A., is the 'Valencia Late' orange cultivar (non-patented in the United States) which is well recognized for its quality fruit.

The new cultivar of *Citrus sinensis* of the present invention was discovered during 1999 as a single branch mutation on a tree of the 'Valenica Late' cultivar at L'Alcudia de Crespins, Valencia, Spain. The discovery was made in a nursery setting consisting of trees of the 'Valencia Late' cultivar. The new cultivar is believed to be a significant mutation of the 'Valencia late' cultivar of unknown causation.

I was primarily attracted to a single plant of the new cultivar in view of its distinctive fruit and leaf characteristics which were substantially different than those of the 'Valencia Late' cultivar. Had I not discovered and preserved the single branch of the new cultivar it would have been lost to mankind.

The new cultivar displays characteristics of both an Orange tree and a Tangerine tree.

It was found that the new Orange Tree of the present invention possesses the following combination of characteristics:

(a) forms attractive large seedless fruit which when compared to that of the 'Valencia Late' cultivar bears a lighter yellow-orange external coloration, a generally more flattened configuration, commonly a greater diameter, and peels more readily, (b) forms larger leaves which generally are more rounded in configuration and less elongated than those of the 'Valencia Late' cultivar, (c) bears late-maturing fruit that matures for consumption at approximately the same time as that of the 'Valencia late' cultivar, and (d) is well suited for the commercial production of a fruit crop.

The new cultivar of the present invention also can be readily distinguished from the 'Nova' cultivar (non-patented in the United States). More specifically, the 'Nova' cultivar forms smaller fruit, and the leaves are smaller and more elongated.

The new cultivar of the present invention has been found to undergo asexual propagation at Valencia, Spain, by the rooting of cuttings and by grafting. Such asexual propagation has been shown that the charateristics of the new cultivar are strictly transmissible from one generation to another. Accordingly, the new cultivar undergoes asexual propagation in a true to type manner.

The new cultivar has been named 'Alvarina'.

BRIEF DESCRIPTION OF THE PHOTOGRAPHS

The accompanying photographs show as nearly true as it is reasonably possible to make in color ilustrations of this character typical specimens of the new variety. The plants were being grown at Valencia, Spain.

FIG. 4 illustrates typical floral buds, as well as an open flower and foliage of the new cultivar.

DETAILED DESCRIPTION

Figure 1:
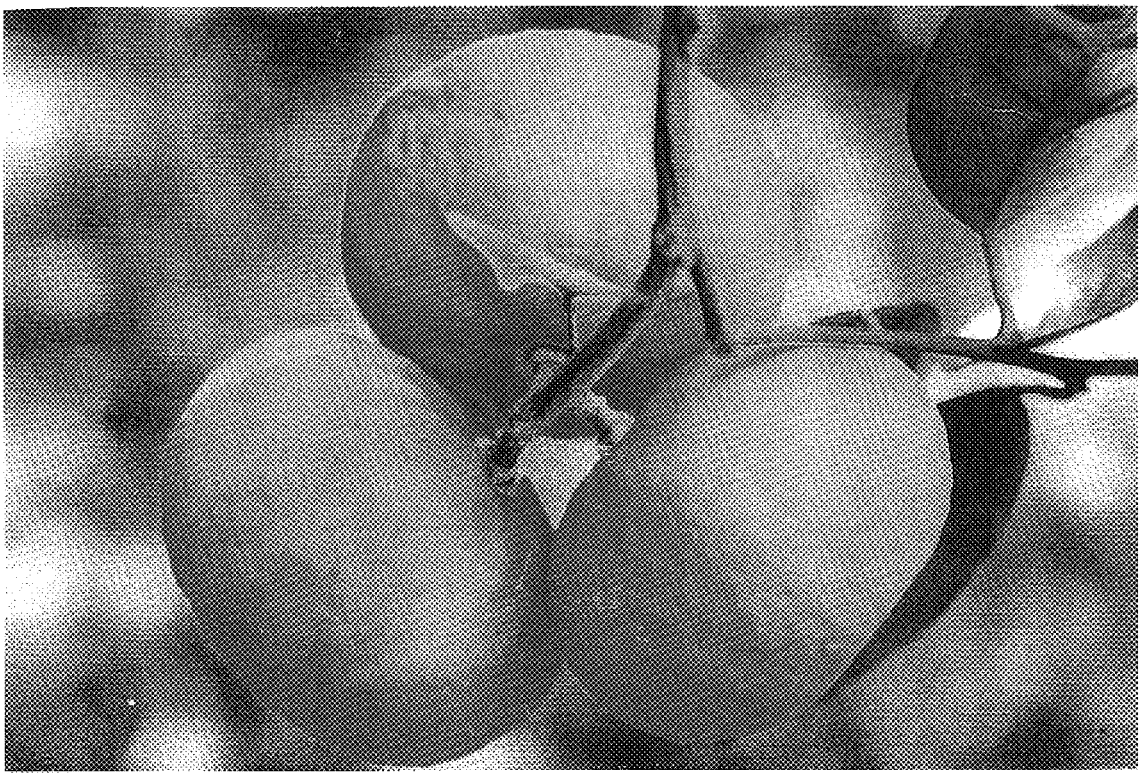
FIG.1 illustrates a cluster of typical fruit wherein the light yellow-orange external coloration and the generally flattened configuration are ilustrated.
Figure 2:
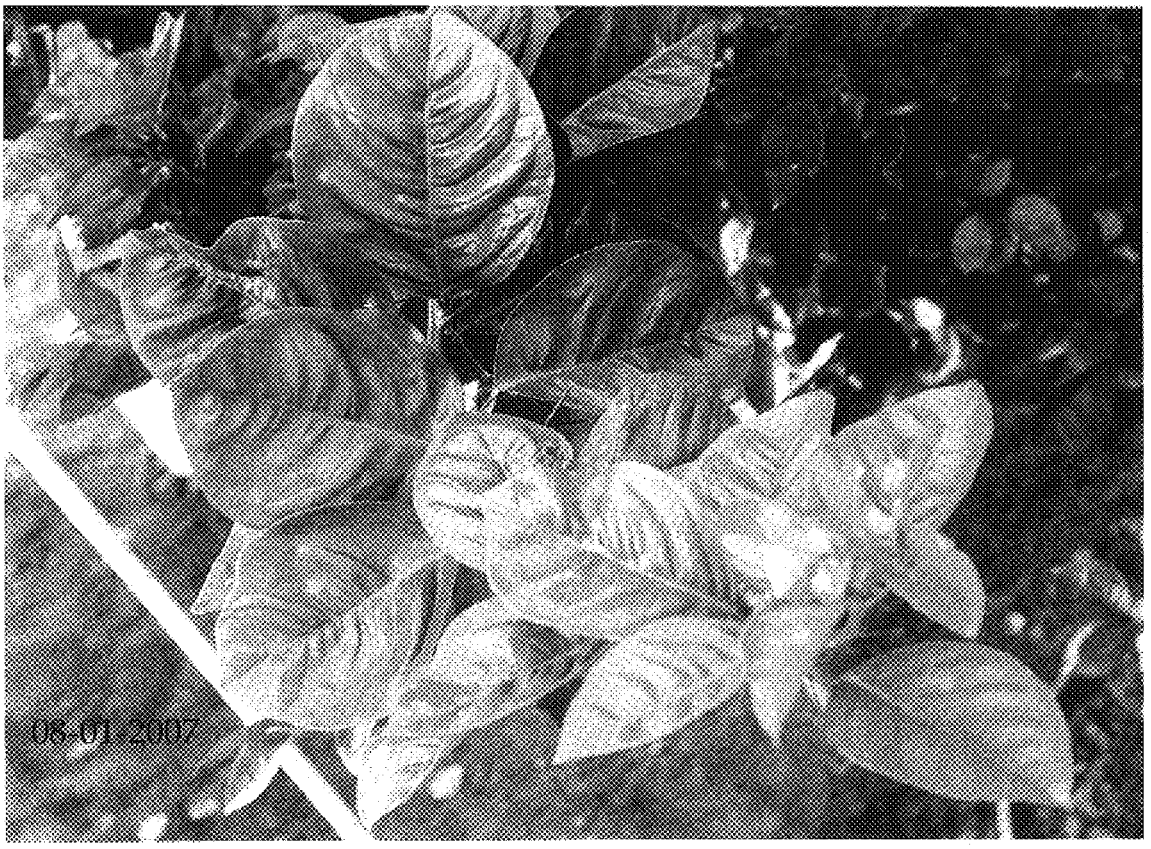
FIG. 2 illustrates the typical foliage of the new cultivar. The generally rounded configuration of the leaves is illustrated.
Figure 3:
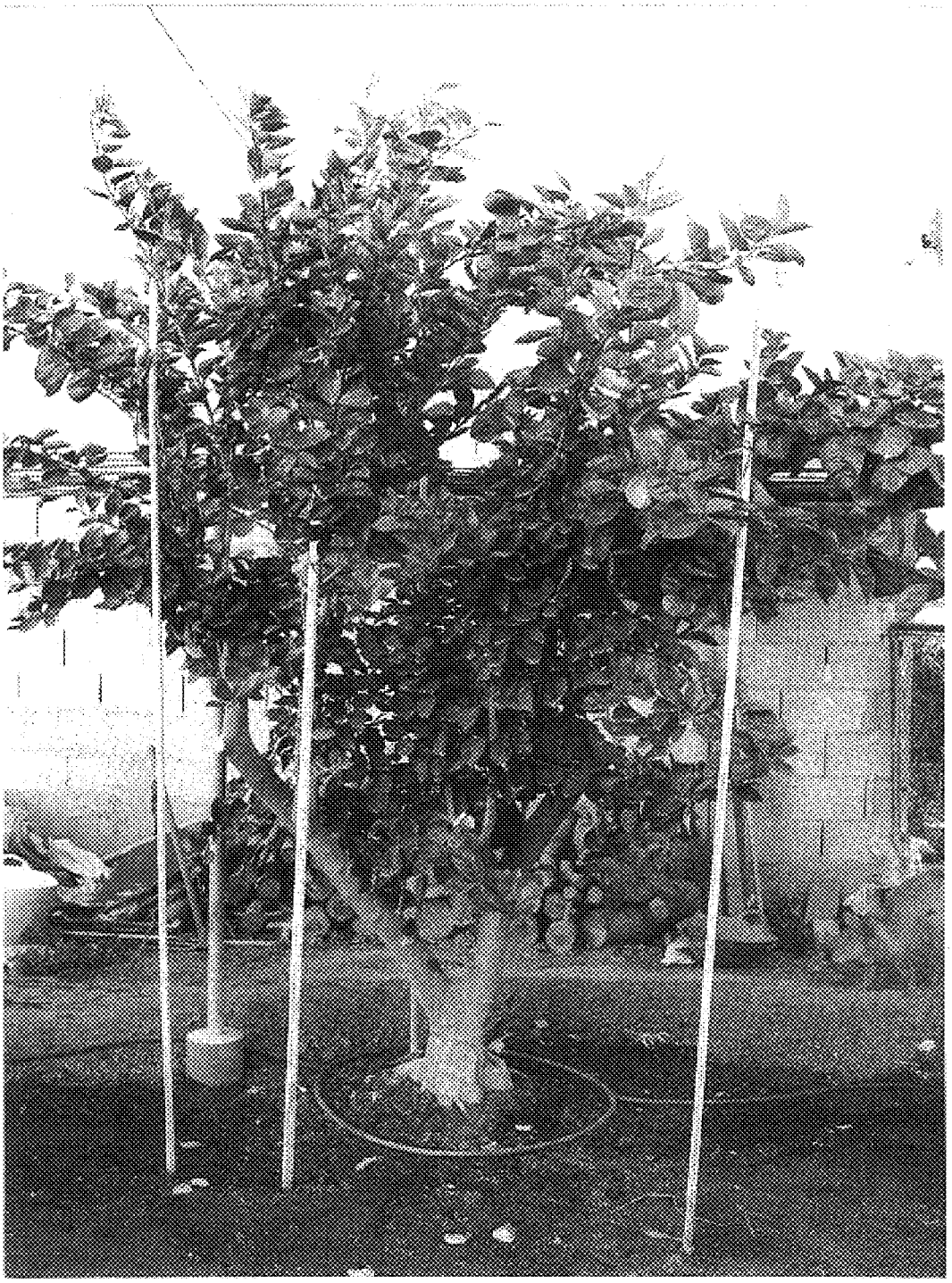
FIG. 3 illustrates the compact growth habit of a typical tree of the new cultivar while grafted on the 'Naval Late' cultivar (non-patented in the United States). The photograph was obtained on Jul. 15, 2005.

The description is based on the observation of plants of the new cultivar having ages of approximately three and five years while growing outdoors at Valencia, Spain. The chart used in the identification of the colors is that of The Royal Horticultural Society (R.H.S. Colour Chart), London, England. Common color terms are to be accorded their customary dictionary significance.

Classification: *Citrus sinensis.*

Tree:

*Growth habit.*—Vigorous and generally compact.

*Height.*—Commonly approximately 2.5 to 3 meters at an age of 3 years.

*Width.*—Very wide, and commonly approximately 2.5 to 3 meters at an age of 3 years.

*Trunk diameter.*—Commonly approximately 12 to 18 cm at an age of 3 years measured 30 cm above the ground.

*Bark.*—Commonly near Greyed-Green Group 197B in coloration.

*Thorn length.*—Commonly approximately 3.5 cm on average.

*Thorn color.*—Commonly near Green Group 140A.

Leaves:

*Size.*—Large, relatively thick, commonly approximately 10 to 12 cm in length on average, and approximately 8 to 10 cm in width on average.

*Configuration.*—Large, rounded and generally elliptic, and larger and more rounded and less elongated than the leaves of the 'Valencia Late' cultivar.

*Apex.*—Generally cuspidate.

*Base.*—Cuneate to obtuse.

*Margin.*—Entire.

*Texture.*—Rugose with some glossiness on the upper surface, and slightly roughened and more rugose on the under suurface.

*Coloration.*—Light to medium brilliant green, commonly near Green Group 140A on both surfaces, but commonly somewhat less brilliant on the under surface.

Inflorescence:

*Time.*—Flowering commonly begins during late March and extends through April at Valencia, Spain.

*Size.*—Commonly approximately 1.5 to 3 cm in diameter.

*Petal number.*—Five.

*Petal size.*—Commonly approximately 0.7 to 1 cm in length on average.

*Petal color.*—Near White Group 155A.

*Fragrance.*—Intense and similar to orange blossoms.

*Calyx size.*—Commonly 1 to 1.2 cm in length on average.

*Calyx color.*—Commonly near Green Group 140A.

Fruit:

*Time of maturity.*—Late, and matures for consumption at approximately the same time as the 'Valencia Late' cultivar.

*Size.*—Large, commonly approximately 4.5 to 5 cm in height and approximately 6.5 to 7 cm in width.

*Configuration.*—Generally flattened unlike the 'Valencia Late' cultivar, commonly of a greater diameter than the 'Valencia Late' cultivar, and similar to that of a Tangerine.

*External coloration.*—Yellow-orange, Orange Group 25C, and generally lighter in coloration than the 'Valencia Late' cultivar.

*Internal flesh coloration.*—Light orange, Orange Group 28C, and generally comparable to that of the 'Valencia Late' cultivar.

*Ability to peel.*—Peels with ease when compared to the 'Valencia Late' cultivar.

*Rind.*—Commonly approximately 0.2 to 0.3 cm in thickness, thinner than that of the 'Valencia Late' cultivar, and more similar to that of a Mandarin.

*Surface texture.*—Moderately smooth and less rugose than that of the 'Valencia Late' cultivar as illustrated in FIG. 1.

*Fruit segments.*—Commonly approximately 10 well-developed segments are exhibited.

*Naval.*—Absent or very rare.

*Parthenocarpy.*—Seedless fruit is formed.

*Eating quality.*—Juicy, and excellent.

*Taste.*—More delicate and generally sweeter than the fruit of the 'Valencia Late' cultivar.

*Productivity.*—A three year-old tree commonly produces approximately 56 to 80 Kg of fruit.

*Stem length.*—Commonly approximately 1 to 1.5 cm.

*Stem color.*—Near Green Group 140A.

*Calyx length.*—Commonly approximately 1 to 1.2 cm.

*Calyx color.*—Near Green Group 140A.

Development:

*Resistance to diseases.*—During observations to date has proven to be highly resistant as confirmed by the Valencian Institute for Agricultural Research (I.V.I.A.), Valencia, Spain, to diseases and viruses that commonly attack orange trees.

*Resistance to insects.*—Appears to be superior in resistance during observations to date perhaps in view of the larger leaf size and thickness.

*Winter hardiness.*—Has withstood temperatures of −4° C.

*Resistance to heat.*—Has withstood temperatures of 46° C.

The new 'Alvarina' cultivar has not been observed under all possible environment conditions to date. Accordingly, it is possible that the phenotypic expression may vary somewhat with changes in light intensity and duration, cultural practices, and other environmental conditions.

I claim:

1. A new distinct *Citrus* plant characterized by the following combination of characteristics:

(a) forms attractive large seedless fruit which when compared to that of the 'Valencia Late' cultivar bears a lighter yellow-orange external coloration, a generally more flattened configuration, commonly a greater diameter, and peels more readily, (b) forms larger leaves which generally are more rounded in configuration and less elongated than those of the 'Valencia Late' cultivar, (c) bears late-maturing fruit that matures for consumption at approximately the same time as the 'Valencia Late' cultivar, and (d) is well suited for the commercial production of a fruit crop;

substantially as herein shown and described.

* * * * *